United States Patent
Patton et al.

(10) Patent No.: US 7,888,521 B2
(45) Date of Patent: Feb. 15, 2011

(54) ALUMINUM CHELATES

(75) Inventors: Jerry R. Patton, Bridgeport, AL (US); Robert W. Alverson, Soddy-Daisy, TN (US)

(73) Assignee: Chattem Chemicals, Inc., Chattanooga, TN (US)

( * ) Notice: Subject to any disclaimer, the term of this patent is extended or adjusted under 35 U.S.C. 154(b) by 170 days.

(21) Appl. No.: 12/309,982

(22) PCT Filed: Aug. 21, 2007

(86) PCT No.: PCT/US2007/018460

§ 371 (c)(1), (2), (4) Date: Mar. 11, 2009

(87) PCT Pub. No.: WO2008/024332

PCT Pub. Date: Feb. 28, 2008

(65) Prior Publication Data

US 2010/0004150 A1 Jan. 7, 2010

Related U.S. Application Data

(60) Provisional application No. 60/840,208, filed on Aug. 24, 2006.

(51) Int. Cl.
*C07C 49/92* (2006.01)
*C07F 5/06* (2006.01)
*C09D 11/00* (2006.01)

(52) U.S. Cl. ............... 556/40; 556/182; 106/31.13; 106/287.17

(58) Field of Classification Search .............. 556/40, 556/182; 106/31.13, 287.17
See application file for complete search history.

(56) References Cited

U.S. PATENT DOCUMENTS 3,014,939 A 12/1961 Kluiber et al.

(Continued)

OTHER PUBLICATIONS

The International Search Report for PCT Application No. PCT/US2007/018460, as published under WO 2008/024332 A3.

(Continued)

*Primary Examiner*—Porfirio Nazario Gonzalez
(74) *Attorney, Agent, or Firm*—Amster, Rothstein & Ebenstein LLP

(57) ABSTRACT

Provided are aluminum chelates having the formula (I). Also provided are compositions having these chelates, methods of producing these chelates, and methods of modifying the viscosity of a liquid or a semisolid using these chelates.

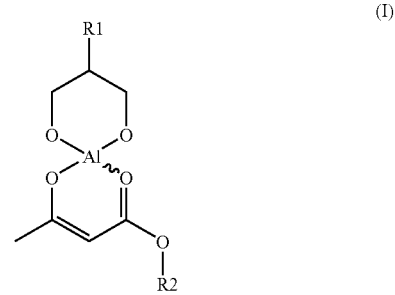

25 Claims, 7 Drawing Sheets

U.S. PATENT DOCUMENTS

| | | |
|---|---|---|
| 3,041,380 A | 6/1962 | Norman |
| 3,956,352 A | 5/1976 | Bouillon et al. |
| 5,306,759 A | 4/1994 | Sakagami et al. |
| 5,427,615 A | 6/1995 | Jordan |
| 5,635,591 A | 6/1997 | Williams et al. |
| 6,887,398 B1 | 5/2005 | Finmans et al. |
| 6,953,863 B2 | 10/2005 | Pratt et al. |

OTHER PUBLICATIONS

The Written Opinion of the International Searching Authority for PCT Application No. PCT/US2007/018460.

Aluminum Isopropoxide

Isopropyl Acetoacetonate

Simple Chelate Intermediate

2-Methyl 1,3 Propane Diol

Compound A

ALUMINUM CHELATES

This is a U.S. national phase of PCT Application No. PCT/US2007/018460, filed Aug. 21, 2007, which claims priority to U.S. Provisional Application No. 60/840,208, filed Aug. 24, 2006.

BACKGROUND OF THE INVENTION (1) Field of the Invention

The present invention generally relates to aluminum chelates. More specifically, the invention provides a class of aluminum chelates that are useful gellants for improving rheological properties of liquids and semi-solids.

(2) Description of the Related Art

REFERENCES

U.S. Pat. No. 1,870,859.
U.S. Pat. No. 2,687,423.
U.S. Pat. No. 2,839,421.
U.S. Pat. No. 2,844,551.
U.S. Pat. No. 2,845,447.
U.S. Pat. No. 2,871,135.
U.S. Pat. No. 2,877,248.
U.S. Pat. No. 3,006,941.
U.S. Pat. No. 3,068,263.
U.S. Pat. No. 3,197,436.
U.S. Pat. No. 3,305,571.
U.S. Pat. No. 3,651,131.
U.S. Pat. No. 3,686,249.
U.S. Pat. No. 3,819,671.
U.S. Pat. No. 3,905,936.
U.S. Pat. No. 3,956,352.
U.S. Pat. No. 4,150,047.
U.S. Pat. No. 4,183,833.
U.S. Pat. No. 4,525,307.
U.S. Pat. No. 4,529,555.
U.S. Pat. No. 4,639,492.
U.S. Pat. No. 5,427,615.
U.S. Pat. No. 5,587,007.
U.S. Pat. No. 5,635,591.
U.S. Pat. No. 5,763,565.
U.S. Pat. No. 5,844,071.
U.S. Pat. No. 6,451,873 B1.
U.S. Pat. No. 6,806,301 B2.
U.S. Pat. No. 6,894,096 B2.
U.S. Pat. No. 6,953,863 B2.

Complex chelates of aluminum derivatives have been known for 20+ years. The reaction of ethyl acetoacetonate with aluminum isopropoxide (AIP) to form a simple chelate produces a fast acting aluminum derivative, which still has two isopropoxide groups on the aluminum moiety. The further reaction of this derivative produces isopropyl alcohol and the evolution of a flammable solvent has been deemed undesirable for ink varnish preparation. Reaction of this simple chelate with a higher boiling alcohol or preferably a diol to replace both isopropyl alcohol groups produces a complex chelate. The most commonly used diols are 1,3 butylene glycol and neopentyl glycol. The reason for the use of 1,3 glycols is the bond length allows each diol to react with one aluminum moiety and helps prevent cross linking between aluminum molecules. This configuration also means that the product will remain a liquid when prepared in ink oils, which is the case in most of the commercial products. The pure compounds are solids and can be dissolved in ink oils for formulation in the varnish manufacture. The mole ratios are 1.0:1.0:0.90-0.99 to 1.0 based on AIP, acetyl acetonates, and diols, respectively. There is a need for additional chelates that improve the rheology of various liquids and solids, in particular inks, greases and varnishes.

SUMMARY OF THE INVENTION

Accordingly, the present invention is based on the development of novel aluminum chelates that provide excellent rheological properties when added to liquids and semi-solids such as inks, greases and varnishes. Thus, the invention is directed to compounds having formula I:

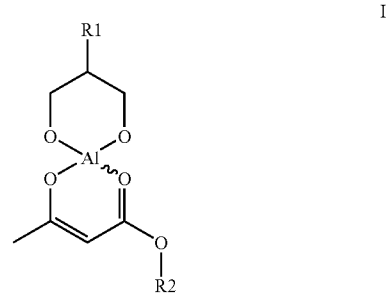

wherein
R1 is H or a C1-C5 straight or branched alkyl, alkenyl or alkynyl and
R2 is propyl, isopropyl, butyl, isobutyl, sec-butyl, tert-butyl, pentyl, isopentyl, tert-pentyl, or neopentyl.

The invention is also directed to compositions comprising the above compounds.

Additionally, the invention is directed to methods of producing an aluminum gellant. The methods comprise
(a) reacting aluminum isopropoxide with a compound having formula II:

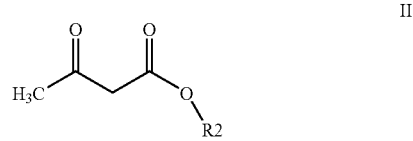

in a manner sufficient to produce an intermediate having formula III:

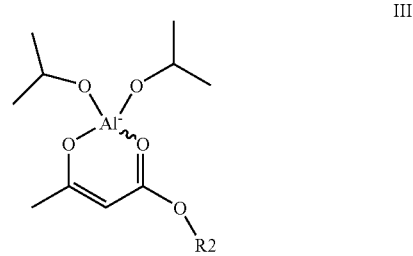

wherein R2 is propyl, isopropyl, butyl, isobutyl, sec-butyl, tert-butyl, pentyl, isopentyl, tert-pentyl, or neopentyl, then
(b) reacting the intermediate having formula III with a compound having formula IV:

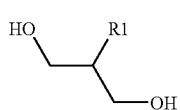

in a manner sufficient to produce a compound of formula I:

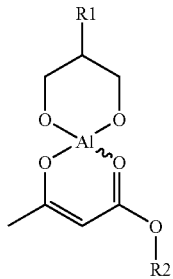

wherein R1 is H or a C1-C5 straight or branched alkyl, alkenyl or alkynyl,

R2 is propyl, isopropyl, butyl, isobutyl, sec-butyl, tert-butyl, pentyl, isopentyl, tert-pentyl, or neopentyl, and wherein the compound of formula I is the aluminum gellant.

The invention is additionally directed to methods of modifying the viscosity of a liquid or a semisolid. The methods comprise adding the above compounds to the liquid or semisolid.

DETAILED DESCRIPTION OF THE INVENTION

Figure 1:
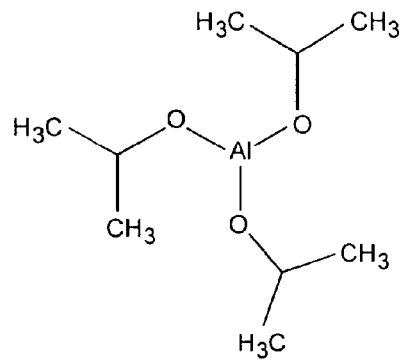
FIG. 1 shows chemical formulas of Compound A and the reagents used to make Compound A.
Figure 1:
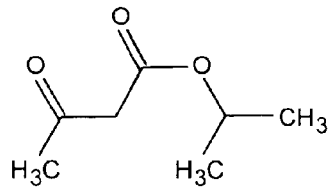
Figure 1:
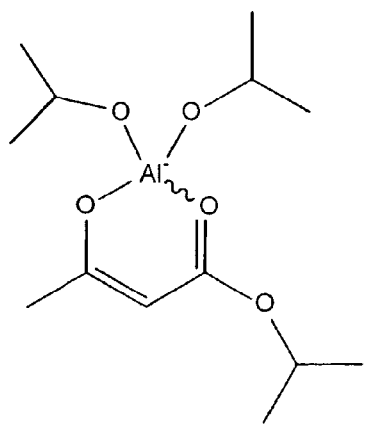
Figure 1:
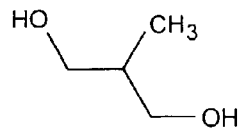
Figure 1:
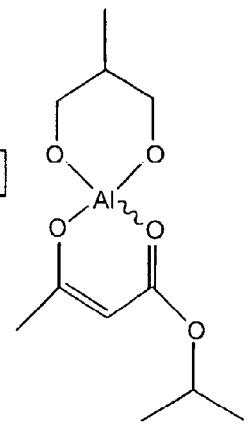
Figure 2:
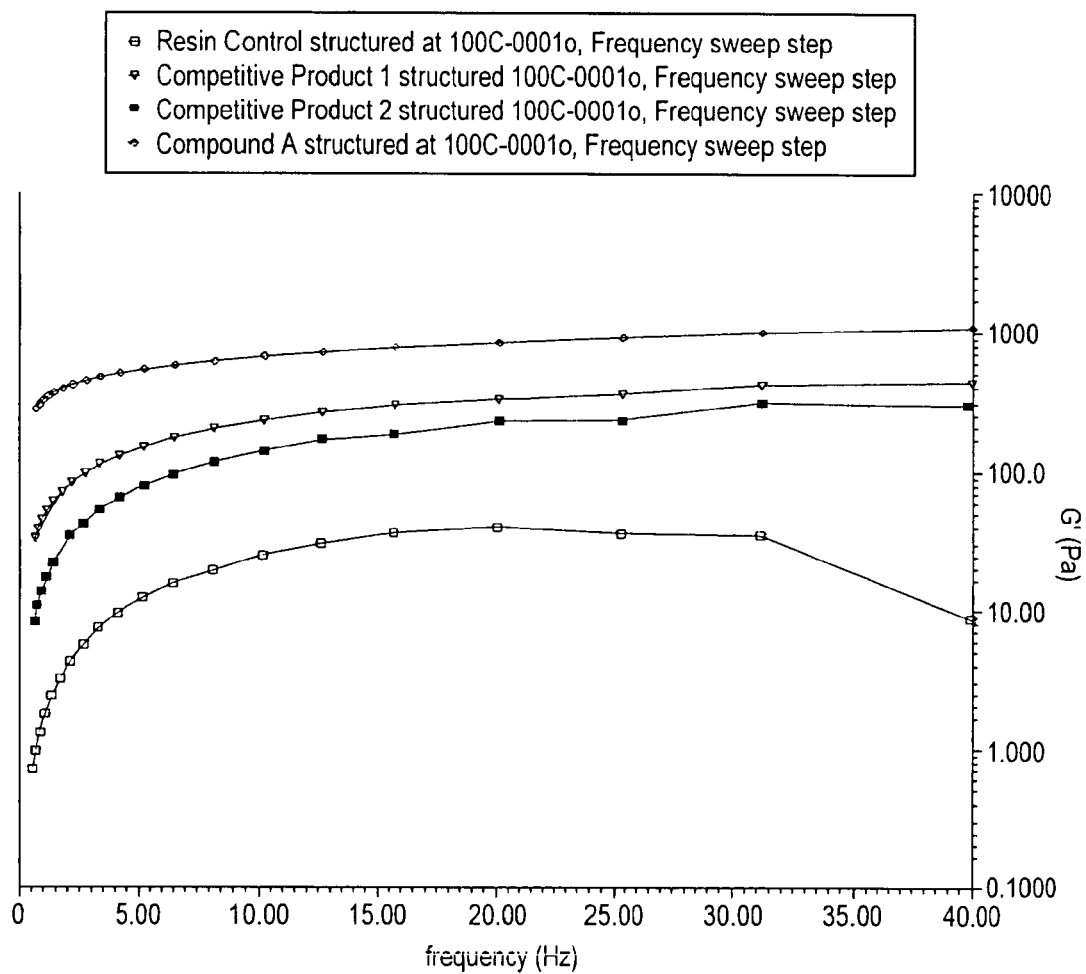
FIG. 2 is a graph of experimental results showing a comparison of the G' of Compound A with commercial structured resins.
Figure 3:
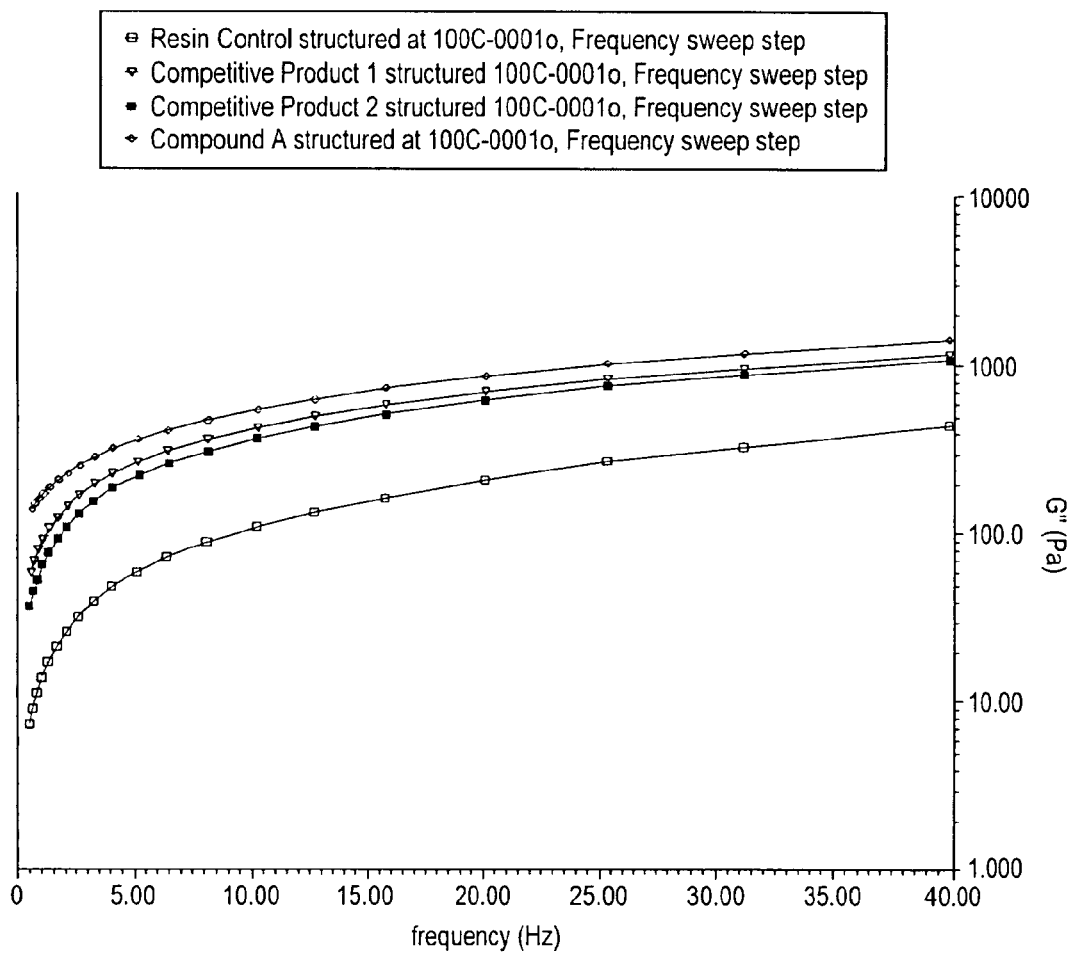
FIG. 3 is a graph of experimental results showing a comparison of the G" of Compound A with commercial structured resins.
Figure 4:
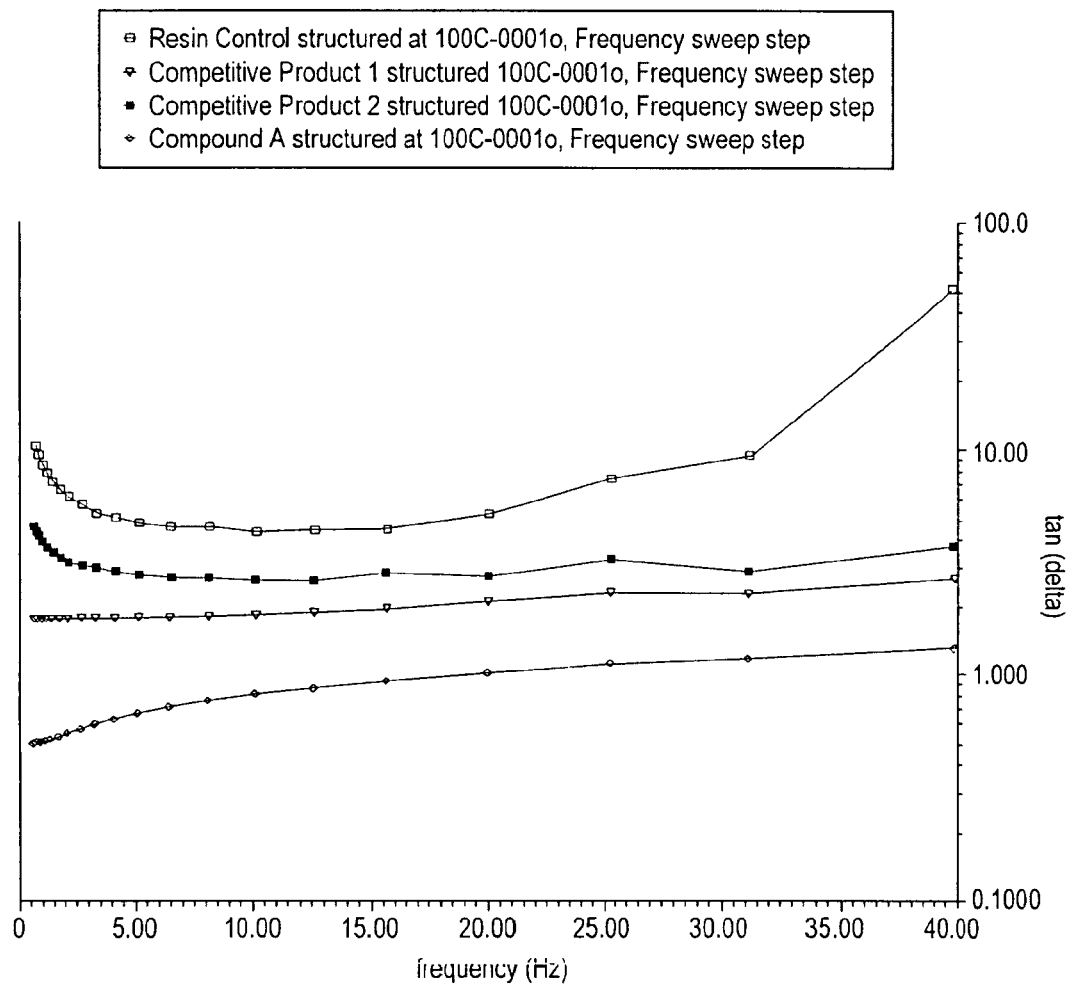
FIG. 4 is a graph of experimental results showing a comparison of the tan(Δ) of Compound A with commercial structured resins.
Figure 5:
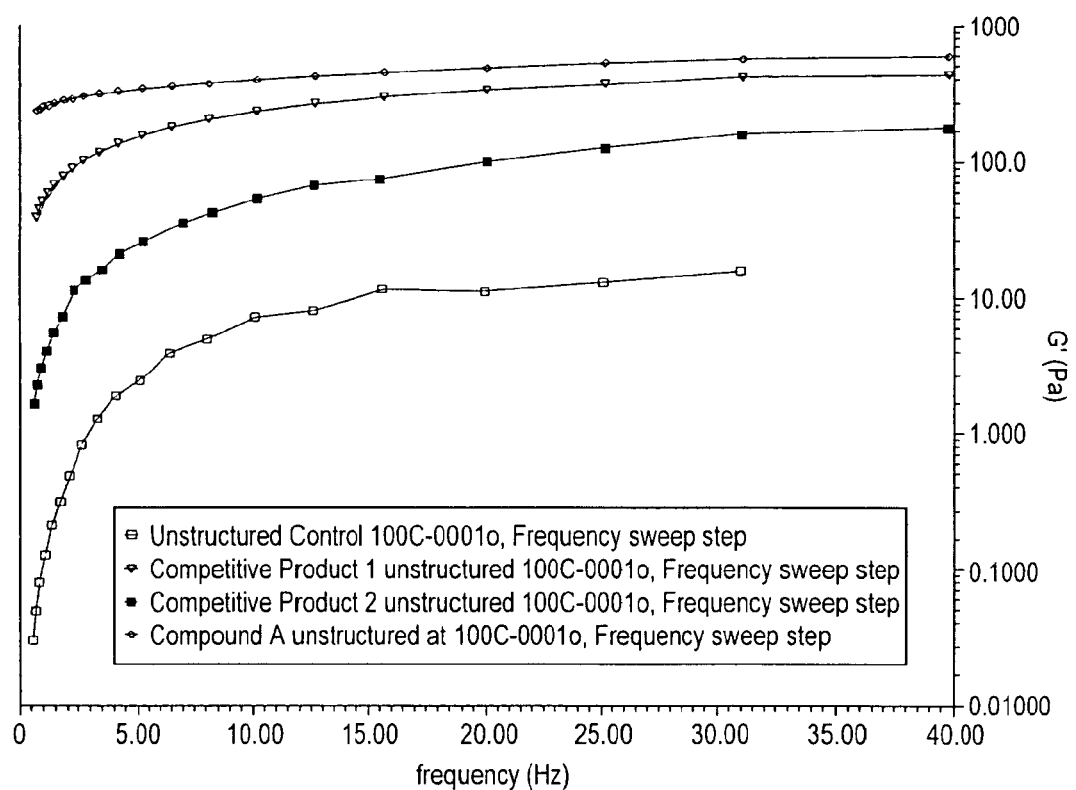
FIG. 5 is a graph of experimental results showing a comparison of the G' of Compound A with commercial unstructured resins.
Figure 6:
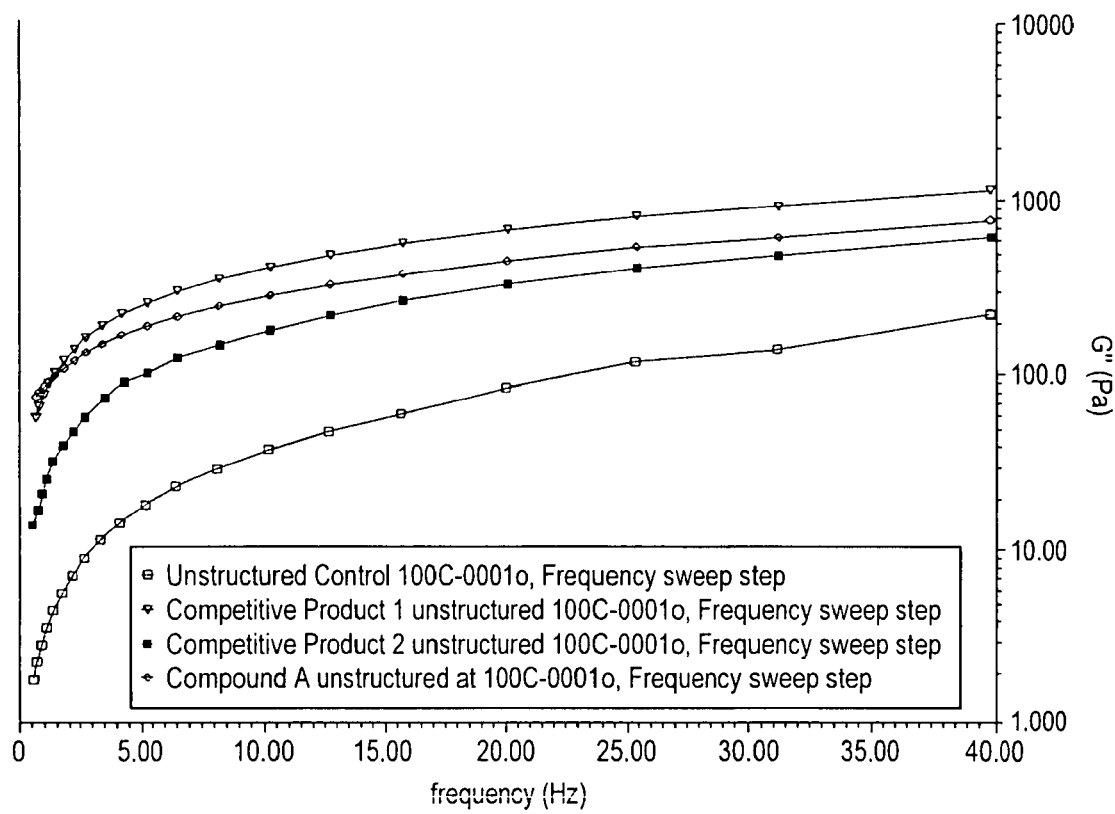
FIG. 6 is a graph of experimental results showing a comparison of the G" of Compound A with commercial structured resins.
Figure 7:
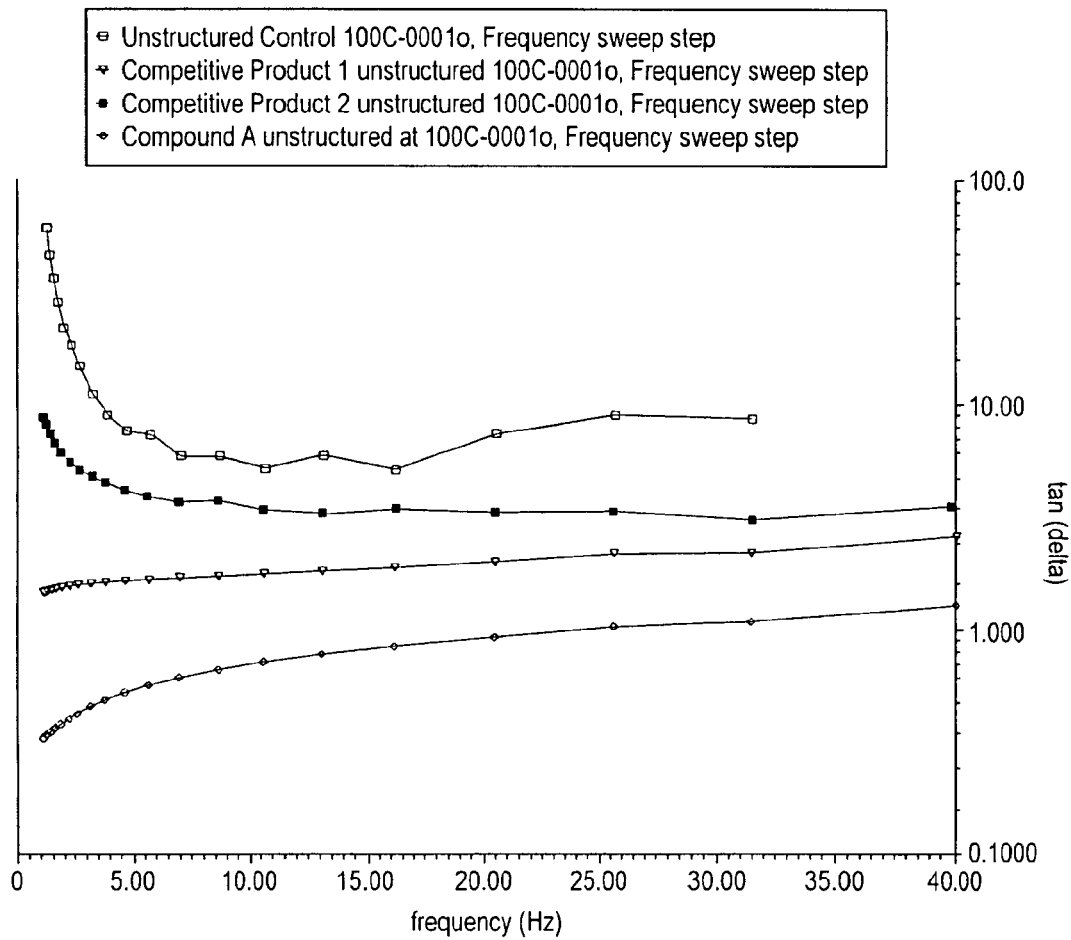
FIG. 7 is a graph of experimental results showing a comparison of the tan(Δ) of Compound A with commercial structured resins.

The present invention is based on the development of novel aluminum chelates that provide excellent rheological properties when added to liquids and semi-solids such as inks, greases and varnishes. See Example. Thus, the invention is directed to compounds having formula I:

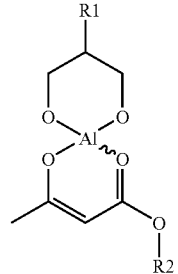

wherein

R1 is H or a C1-C5 straight or branched alkyl, alkenyl or alkynyl and

R2 is propyl, isopropyl, butyl, isobutyl, sec-butyl, tert-butyl, pentyl, isopentyl, tert-pentyl, or neopentyl.

Preferably, R1 in these compounds is methyl. A preferred moiety for R2 is isopropyl. Most preferably, the compound (Compound A) has the formula

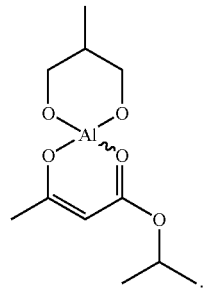

See Example, establishing the useful rheological properties of this compound.

These compounds are useful as gellants in liquids or semisolids. As shown in the Example, the above preferred compound had superior rheological properties when incorporated into a structured or unstructured resin, when compared with two commercial gellants. Rheological properties can be determined for any of the invention compounds by determining the G', G" and Tan Δ characteristics of products having the compound. As is known in the art, G' is the elastic modulus, G" is the viscous modulus, and Tan Δ is G"/G'. These characteristics can be measured without undue experimentation by methods known in the art (see, e.g., Handbook of Elementary Rheology by H. Barnes, University of Wales, 2000).

The invention is also directed to compositions comprising the above compounds. Preferably, the composition is a liquid or semisolid. As used herein, a semisolid is a composition that is intermediate in rigidity between a solid and a liquid. Examples include a grease, a paste and a gel. A preferred liquid in these embodiments is an oil, and preferably an ink. A preferred semisolid is a grease. The compounds are also useful in coatings, such as a paint or, preferably, a varnish.

Additionally, the invention is directed to methods of producing an aluminum gellant. The methods comprise (a) reacting aluminum alkoxide with a compound having formula II:

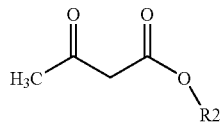

II in a manner sufficient to produce an intermediate having formula III:

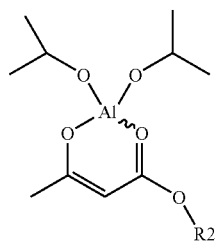

III wherein R2 is propyl, isopropyl, butyl, isobutyl, sec-butyl, tert-butyl, pentyl, isopentyl, tert-pentyl, or neopentyl, then (b) reacting the intermediate having formula II with a compound having formula IV:

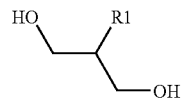

IV in a manner sufficient to produce a compound of formula I:

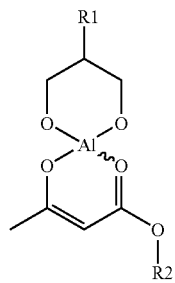

I wherein R1 is H or a C1-C5 straight or branched alkyl, alkenyl or alkynyl,

R2 is propyl, isopropyl, butyl, isobutyl, sec-butyl, tert-butyl, pentyl, isopentyl, tert-pentyl, or neopentyl, and wherein the compound of formula I is the aluminum gellant.

In these steps, a preferred range of the ratio of the reagents is 1.0:1.0:0.90-1.0:1.0:1.0 aluminum isopropoxide:compound II:compound IV. The most preferred ratio is 1.0:1.0:0.95.

Without being bound to any particular mechanism, it is believed that the invention choices of the β-dicarbonyl (i.e., the choice of R2 in that reagent) is superior to the prior art ethyl acetoacetate reagent because the trans-esterification step (a) product (III) is important to the performance of the final product.

Preferably, R1 in these compounds is methyl. A preferred moiety for R2 is isopropyl. Most preferably, the compound has the formula

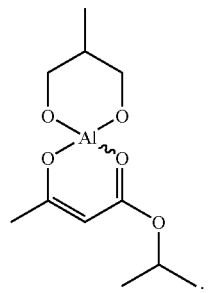

Subsequent to production of the invention compound, it can be directly added to an oil, a grease or a coating.

The invention is additionally directed to methods of modifying the viscosity of a liquid or a semisolid. The methods comprise adding any of the above compounds to the liquid or semisolid. Preferably, the compound has the formula

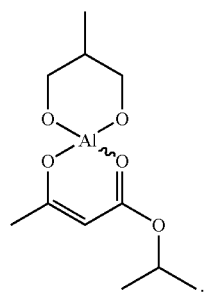

Preferred liquids or semisolids for these methods includes inks, greases and coatings.

Preferably, the compound is added to the liquid or semisolid to a concentration of less than about 3% on a weight basis. More preferably, the compound is added to the liquid or semisolid to a concentration of between about 0.1% to 2.0%, most preferably between about 0.4% and 1.5% on a weight basis.

Preferred embodiments of the invention are described in the following example. Other embodiments within the scope of the claims herein will be apparent to one skilled in the art from consideration of the specification or practice of the invention as disclosed herein. It is intended that the specification, together with the example, be considered exemplary only, with the scope and spirit of the invention being indicated by the claims, which follow the example.

Example

The aluminum content has a direct relationship on the rheology of the varnishes prepared even though the percentage of the aluminum gellant in the formulation is usually ~1%. From this relationship, the lower the molecular weight of the ingredients, the higher the aluminum content so the starting materials for the new product (Compound A) were chosen to optimize the aluminum content and keep the desired rheology in the finished varnish.

The inventors have developed a new gellant, Compound A (FIG. 1), which is a complex chelate prepared using isopropyl acetoacetonate as the simple chelate portion and 2-methyl 1,3 propane diol as the alcohol (diol) portion of the aluminum complex chelate (FIG. 1). Both of these components were chosen to enhance the rheology of the varnishes prepared when as little as 0.1%-0.4% of the aluminum gellant is employed. Isopropyl acetoacetonate and 2-methyl 1,3-propane diol, individually and in the aggregate, produce a superior gellant when compared to all other combinations examined. The most efficient variant was produced when these components were in a 1.0:1.0:0.95 molar ratio.

Compound A has a flash point above 230° F., is stable when stored as an ink oil mixture, has an activation temperature between 80° F. and 220° F., and produces a rheological advantage when compared to all of the complex chelates on the market using ethyl acetoacetate. A preferred activation temperature is 160° F.-180° F. The solid product has been prepared and diluted in different ink oils for incorporation into varnish systems. The rheology produced when a structured resin is employed gives a better viscous and elastic modulus than the structured resin without the aluminum derivative, and when a non-structured resin is used, a boost in rheology up above that of a structured resin (without an aluminum gellant) is seen.

Comparison of varnishes at 100° C. shows the advantage of Compound A compared to other products on the market. See FIGS. 2-7 for comparisons of the structured and unstructured resins made with three aluminum gellants. Compound A shows a distinct advantage over the commercial products tested. All complex chelates and acylates at the same concentration of the aluminum gellant as our new product are ~one fifth as potent, when comparing the G', and G".

The advantages to the ink varnish manufacturer and the printer include enhanced rheological properties at a lower dosing concentration. The product can be produced in nearly any desired ink oil or as a solid and diluted in a customer-specific oil for custom applications. The addition of aluminum gellants adds to the gloss in varnish vehicles as well as enhancing the water emulsification capabilities. The Compound A gellant offers these advantages along with the rheological properties desired in both structured and unstructured resins.

The evolution of the resins to prepare varnishes for the ink industry has taken several turns over the past fifteen years. The original unstructured resins had a set acid value ~25 and were variable in the hydroxyl groups present. When structured resins showed in the marketplace, there was a great variability since the higher molecular weight resins varied during manufacture. The advent of structured resin solutions gave the resin manufacturer an advantage since they could now quench the reaction and offer a homogeneous mixture, even though the resin may contain flaws, it was consistent.

The purification procedures employed by some structured resin manufacturers in the Pacific rim countries, now produces a flake product, which has better rheological attributes than the resin solutions produced in the United States. The addition of an aluminum gellant to these varnish vehicles enhances the rheology, gloss and water emulsification. While Compound A was developed to optimize these advantages with the newer resins, it works for the older structured and unstructured resins, as well.

One of the complaints of varnish makers over the past decade is the presence of "gel seeds" when the varnish is prepared. These particulates are usually removed by filtration before the varnishes reach the ink manufacturers. Compound A produces less gel seeds than conventional additives, which is an advantage over the commercial chelates and acylates on the market today.

Some varnish manufacturers will find Compound A to be more effective by incorporating the material as a solid, while others will want the material diluted with their specific ink oil. Both can be accommodated. Varnish vehicles prepared from several different resins have shown that XCP-1098 is 30% to 40% more effective (lower dosing percentages) in producing better rheology than the acylates and complex chelates now in the market place.

The structural formula and reaction sequence is shown in FIG. 1. The rheograms for both structured and unstructured resins comparing Compound A with two commercial aluminum gellants at 100° C. are provided as FIGS. 2-7.

The rheology comparisons of Compound A addition to both structured and unstructured free flow varnishes have been compared to most of the commercial products in the market today. In all cases, Compound A addition showed an advantage of significant magnitude over the commercial chelates as well as the acylates. Different ink oils were used for dilution of Compound A and the rheology differences seen were insignificant at constant aluminum content.

Based on the above, Compound A is a superior aluminum gellant for use in the ink varnish preparation. Physical properties of Compound A are provided in Table 1.

TABLE 1

| Compound A Properties | |
|---|---|
| Molecular Weight | 258 grams/mole |
| Formula | $C_{11}H_{19}O_5Al$ |
| Aluminum Content | 10.5% |
| Flash Point | >230° F. |
| Activation Temperature | 80-220° F., preferably 160-180° F. |

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound having formula I:

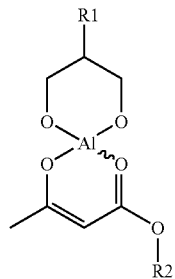

wherein
R1 is H or a C1-C5 straight or branched alkyl, alkenyl or alkynyl and
R2 is propyl, isopropyl, butyl, isobutyl, sec-butyl, tert-butyl, pentyl, isopentyl, tert-pentyl, or neopentyl.

2. The compound of claim 1, wherein R1 is methyl.

3. The compound of claim 1, wherein R2 is isopropyl.

4. The compound of claim 1, wherein the compound has the formula

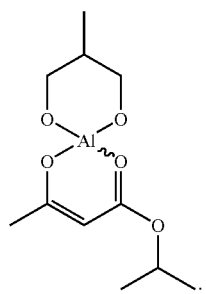

5. A composition comprising the compound of claim 1.

6. The composition of claim 5, which is a liquid or semisolid.

7. The composition of claim 6, wherein the liquid or semisolid is an oil.

8. The composition of claim 7, which is an ink.

9. The composition of claim 6, wherein the liquid or semisolid is a grease.

10. The composition of claim 6, wherein the liquid or semisolid is a coating.

11. The composition of claim 10, which is a varnish.

12. A method of producing an aluminum gellant, the method comprising
(a) reacting aluminum alkoxide with a compound having formula II:

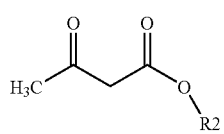

in a manner sufficient to produce an intermediate having formula III:

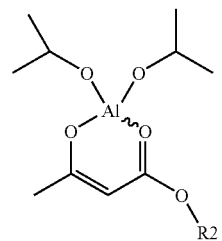

wherein R2 is propyl, isopropyl, butyl, isobutyl, sec-butyl, tert-butyl, pentyl, isopentyl, tert-pentyl, or neopentyl, then
(b) reacting the intermediate having formula III with a compound having formula IV:

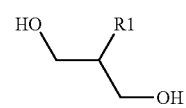

in a manner sufficient to produce a compound of formula I:

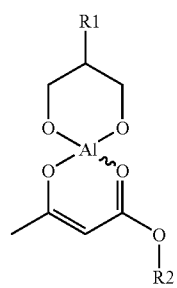

wherein R1 is H or a C1-C5 straight or branched alkyl, alkenyl or alkynyl,
R2 is propyl, isopropyl, butyl, isobutyl, sec-butyl, tert-butyl, pentyl, isopentyl, tert-pentyl, or neopentyl, and
wherein the compound of formula I is the aluminum gellant.

13. The method of claim 12, wherein R1 is methyl.

14. The method of claim 12, wherein R2 is isopropyl.

15. The method of claim 12, wherein the aluminum gellant has the formula

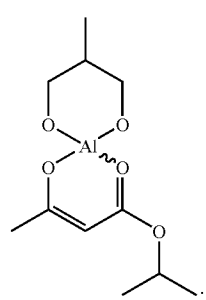

16. The method of claim 12, further comprising adding the aluminum gellant to an oil, a grease or a coating.

17. A method of modifying the viscosity of a liquid or a semisolid, the method comprising adding the compound of any of claims 1-4 to the liquid or semisolid.

18. The method of claim 17, wherein the compound has the formula

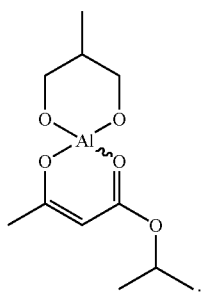

19. The method of claim 17, wherein the liquid or semisolid is an ink, a grease or a coating.

20. The method of claim 19, wherein the ink, grease or coating is an ink.

21. The method of claim 19, wherein the ink, grease or coating is a grease.

22. The method of claim 19, wherein the ink, grease or coating is a coating.

23. The method of claim 17, wherein the compound is added to the liquid or semisolid to a concentration of less than about 3% on a weight basis.

24. The method of claim 17, wherein the compound is added to the liquid or semisolid to a concentration of between about 0.1% and 2.0% on a weight basis.

25. The method of claim 17, wherein the compound is added to the liquid or semisolid to a concentration of between about 0.4% and 1.5% on a weight basis.

* * * * *